United States Patent [19]

Shaw

[11] 4,126,685

[45] Nov. 21, 1978

[54] 6-ARYL-PYRROLO[1,2,9]IMIDAZOLE DERIVATIVES WHICH POSSESS ANTI-HYPERTENSIVE ACTIVITY

[75] Inventor: Andrew Shaw, Macclesfield, England

[73] Assignee: Imperial Chemical Industries Limited, London, England

[21] Appl. No.: 797,349

[22] Filed: May 16, 1977

Related U.S. Application Data

[62] Division of Ser. No. 652,060, Jan. 26, 1976, Pat. No. 4,046,898.

[30] Foreign Application Priority Data

Jan. 31, 1975 [GB] United Kingdom ................ 4303/75

[51] Int. Cl.$^2$ .................. A61K 31/44; A61K 31/415; C07D 487/04
[52] U.S. Cl. .................................... 424/258; 546/271; 546/15; 424/273 R; 424/263; 424/78; 548/324
[58] Field of Search ................... 548/324; 260/296 B, 260/295 K, 286 R, 287 D, 287 T, 288 CE; 424/263, 273, 258

[56] References Cited

PUBLICATIONS

Alekseeva et al., Chemical Abstracts, vol. 77, (1972), 61153p.
Kochergin et al., Chemical Abstracts, vol. 64, (1966), 19593-19594.

*Primary Examiner*—Richard L. Raymond
*Attorney, Agent, or Firm*—Cushman, Darby & Cushman

[57] ABSTRACT

6-Arylpyrrolo[1,2-a]imidazole derivatives, processes for their manufacture, pharmaceutical compositions containing them and a method of using them to lower blood pressure in warm-blooded animals. Representative of the compounds disclosed is 6-(2,6-dichlorophenyl)-2,3,6,7-tetrahydro-5H-pyrrolo[1,2-a]imidazole.

6 Claims, No Drawings

6-ARYL-PYRROLO[1,2,9]IMIDAZOLE DERIVATIVES WHICH POSSESS ANTI-HYPERTENSIVE ACTIVITY

This is a division of application Ser. No. 652,060, filed Jan. 26, 1976, now U.S. Pat. No. 4,046,898.

This invention relates to novel heterocyclic compounds and more particularly it relates to novel 6-aryl-pyrrolo[1,2-a]imidazole derivatives which possess antihypertensive activity.

According to the invention there is provided a compound of the formula:

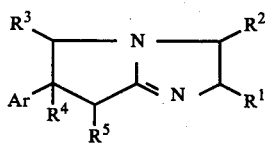

wherein $R^1$, $R^2$, $R^3$ and $R^5$, which may be the same or different, each stands for the hydrogen atom or for an alkyl radical of up to 4 carbon atoms, and wherein either $R^4$ stands for the hydrogen atom or for an alkyl radical of up to 4 carbon atoms and Ar stands for an aromatic nucleus which may optionally bear one or more substituents, or Ar stands for an aromatic nucleus which bears a substituent in the position adjacent to the linking position which substituent together with the substituent $R^4$ forms an alkylene radical of up to 3 carbon atoms, and which nucleus Ar may optionally bear one or more further substituents; or an acid-addition salt thereof.

It will be observed that the compound of the invention possesses at least one asymmetric carbon atom, namely that at the 6- position of the pyrrolo[1,2-a]imidazole which is numbered as follows:

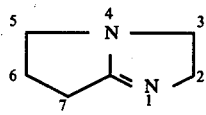

and that it may possess more than one asymmetric carbon atom if any one of the substituents $R^1$, $R^2$, $R^3$ and $R^5$ stands for an alkyl radical. The compound will therefore exist in at least one racemic and at least one pair of optically-active forms. It is to be understood that the invention encompasses the racemic form and any optically-active form which possesses antihypertensive activity, it being a matter of common general knowledge how a racemic compound may be separated into its optically-active forms and how the antihypertensive activity of any particular form may be measured.

A suitable value for $R^1$, $R^2$, $R^3$, $R^4$ or $R^5$ when it stands for an alkyl radical is, for example, the methyl radical.

The aromatic nucleus may be, for example, the phenyl, naphthyl, thienyl, pyridyl or furyl nucleus and it may be unsubstituted or it may bear one or more substituents, for example one, two or three substituents, selected from halogen atoms, for example fluorine, chlorine and bromine atoms, amino, nitro and trifluoromethyl radicals, and alkyl, alkoxy, acylamino and dialkylamino radicals each of up to 6 carbon atoms, for example methyl, ethyl, methoxy, ethoxy, acetamido, dimethylamino and diethylamino radicals.

A suitable value for the alkylene radical formed by $R^4$ together with the substituent in the aromatic nucleus Ar is, for example, the methylene, ethylene, ethylidene or trimethylene radical.

A preferred compound of the invention has the formula given above wherein either:

(a) $R^1$, $R^2$, $R^3$, $R^4$ and $R^5$ all stand for hydrogen atoms and Ar stands for a phenyl radical which bears a substituent in the 2- position which is a fluorine, chlorine or bromine atom or an alkyl radical of up to 4 carbon atoms, and which bears a substituent in the 6- position which is a fluorine, chlorine or bromine atom, a trifluoromethyl radical or an alkyl or alkoxy radical each of up to 4 carbon atoms, and which may optionally bear a substituent in the 3- position which is a fluorine, chlorine or bromine atom, an amino radical or an alkyl or alkoxy radical each of up to 4 carbon atoms; or (b) $R^1$, $R^2$, $R^3$, $R^4$ and $R^5$ all stand for hydrogen atoms and Ar stands for a 1-naphthyl radical which bears a substituent in the 2- position which is a fluorine, chlorine or bromine atom or an alkyl radical of up to 4 carbon atoms; or (c) $R^1$, $R^2$, $R^3$ and $R^5$ all stand for hydrogen, Ar stands for a phenyl radical and $R^4$ together with the substituent in the 2- position of the phenyl radical form the ethylene radical, which phenyl radical Ar may optionally bear a further substituent in the 3- or 6- position which is a fluorine, chlorine or bromine atom, a trifluoromethyl radical or an alkyl or alkoxy radical each of up to 4 carbon atoms; or is an acid-addition salt thereof.

A particularly preferred compound of the invention has the formula given above wherein $R^1$, $R^2$, $R^3$, $R^4$ and $R^5$ all stand for hydrogen and Ar stands for a phenyl radical which bears a chloro or methyl substituent in the 2- position and a fluoro, chloro, bromo, trifluoromethyl, methyl or methoxy substituent in the 6- position, or is an acid-addition salt thereof.

Specific compounds of the invention are hereinafter described in the Examples. A particularly preferred specific compound of the invention is 6-(2,6-dichlorophenyl)-2,3,6,7-tetrahydro-5H-pyrrolo[1,2-a]imidazole or 6-(2-chloro-6-fluorophenyl)-2,3,6,7-tetrahydro-5H-pyrrolo[1,2-a]imidazole or an acid-addition salt thereof.

A suitable acid-addition salt of a compound of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, βnaphthoate, adipate or 1,1-methylene-bis-(2-hydroxy-3-naphthoate), or a salt derived from an acidic synthetic resin, for example a sulphonated polystyrene resin.

According to a further feature of the invention there is provided a process for the manufacture of the compound of the invention which comprises the cyclisation of a compound of the formula:

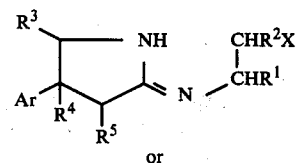

or

-continued

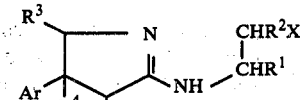

or

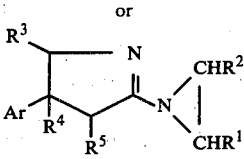

wherein Ar, $R^1$, $R^2$, $R^3$, $R^4$ and $R^5$ have the meanings stated above and wherein X stands for a displaceable radical.

A suitable value for X is, for example, a halogen atom, for example the chlorine, bromine or iodine atom, or the hydroxy radical, or a sulphonyloxy radical, for example the methanesulphonyloxy or toluene-p-sulphonyloxy radical.

When X is a halogen atom or a sulphonyloxy radical, the reaction is preferably carried out under basic conditions, for example in the presence of an alkali metal carbonate or bicarbonate. When X is the hydroxy radical the reaction is preferably carried out under acidic conditions at an elevated temperature. When an aziridine starting material is used, the reaction is preferably carried out under weakly acidic conditions at an elevated temperature.

The starting material may be obtained by the reaction of a pyrroline derivative of the formula:

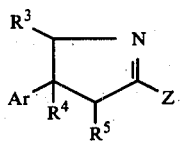

wherein Ar, $R^3$, $R^4$ and $R^5$ have the meanings stated above and wherein Z stands for a displaceable radical, with a compound of the formula:

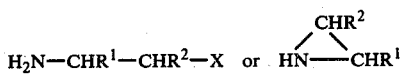

wherein $R^1$, $R^2$ and X have the meanings stated above. Z may be, for example, a halogen atom or an alkoxy or alkylthio radical, for example the ethoxy or methylthio radical, and the pyrroline derivative itself may be obtained by conventional means by reaction of a compound of the formula Z-H, wherein Z has the meaning stated above, under acidic conditions with a pyrrolidinone derivative of the formula:

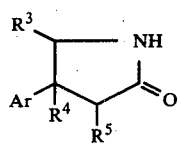

wherein Ar, $R^3$, $R^4$ and $R^5$ have the meanings stated above. The last-mentioned compound wherein Ar is phenyl or substituted phenyl and $R^3$, $R^4$ and $R^5$ are all hydrogen is known from U.K. Specification No. 1,140,188 and from various references cited therein, and other compounds of this type may be made by analogous means. Detailed synthetic methods for the preparation of these intermediates are hereinafter described in the Examples.

According to a further feature of the invention there is provided a process for the manufacture of the compound of the invention which comprises the cyclisation of a compound of the formula:

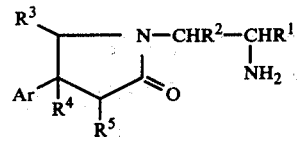

wherein Ar, $R^1$, $R^2$, $R^3$, $R^4$ and $R^5$ have the meanings stated above.

The cyclisation may be carried out under acidic conditions, preferably in the presence of a dehydrating agent, for example phosphorus oxychloride, and it may be carried out at laboratory temperature.

The starting material may be obtained by the reaction of a pyrrolidinone derivative of the formula given above with a compound of the formula:

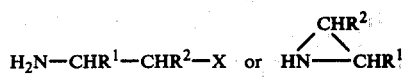

wherein $R^1$, $R^2$ and X have the meanings stated above. Alternatively, when $R^1$ stands for the hydrogen atom the starting material may be obtained by reaction of the said pyrrolidinone derivative with a compound of the formula $CN-CHR^2-X$, wherein $R^2$ and X have the meanings stated above, followed by reduction of the cyano group.

According to a further feature of the invention there is provided a process for the manufacture of the compound of the invention which comprises the cyclisation of a compound of the formula:

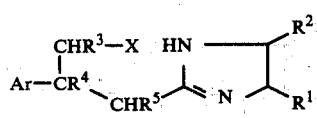

wherein Ar, $R^1$, $R^2$, $R^3$, $R^4$, $R^5$ and X have the meanings stated above.

When X is a halogen atom the reaction is preferably carried out under basic conditions, for example in the presence of an alkali metal carbonate or bicarbonate.

According to a further feature of the invention there is provided a process for the manufacture of a compound of the invention which comprises the cyclisation of a compound of the formula:

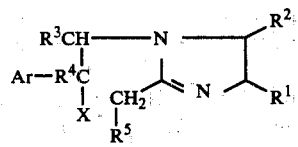

wherein Ar, $R^1$, $R^2$, $R^3$, $R^4$, $R^5$ and X have the meanings stated above.

The cyclisation is preferably carried out by means of a strong base, for example lithium di-isopropylamide or sodium hydride.

According to a further feature of the invention there is provided a process for the manufacture of a compound of the invention which comprises the hydrolysis and decarboxylation of an ester of the formula:

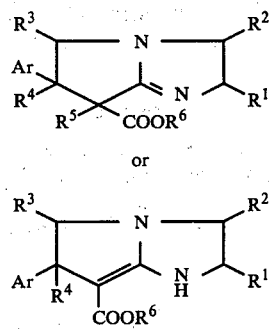

or wherein Ar, $R^1$, $R^2$, $R^3$, $R^4$ and $R^5$ have the meanings stated above and wherein $R^6$ stands for an alkyl radical of up to 6 carbon atoms, for example the methyl or ethyl radical.

The hydrolysis may be carried out in the presence of a base, for example an alkali metal carbonate, in alcoholic or aqueous alcoholic conditions, and the decarboxylation and, if necessary, rearrangement of the double bond then take place spontaneously.

It is to be understood that a compound of the invention wherein the substituent Ar bears a nitro substituent may be converted by reduction into the corresponding compound of the invention wherein Ar bears an amino substituent, and that a latter such compound may be converted by acylation into the corresponding compound of the invention wherein Ar bears an acylamino substituent.

Optically-active enantiomorphs of the compound of the invention may be obtained by the resolution by conventional means of the corresponding racemic compound of the invention. Alternatively, a process of the invention may be carried out using optically-active starting materials.

The compound of the invention in free-base form may be converted into an acid-addition salt thereof by reaction with an acid by conventional means.

As stated above, the compound of the invention possesses antihypertensive activity. This may be demonstrated by its effect, after oral or intravenous administration, in lowering the blood pressure of renal hypertensive dogs or rats, these being standard test animal preparations for the measurement of antihypertensive activity. The compound is also effective in lowering the blood pressure of a dog when administered directly into the lateral ventricle of the dog's brain. At a dose of the compound which produces effective lowering of blood pressure in a dog or rat, no symptoms of toxicity are apparent.

The compound of the invention possesses a qualitatively similar type of antihypertensive activity to that possessed by the known clinically-effective antihypertensive agent clonidine. However, a preferred compound of the invention has much less sedative effect than clonidine, the sedative effect of clonidine being a known and clinically-undesirable side effect of that compound.

The antihypertensive and sedative activities of a selection of compounds of the invention may be measured as follows:

Antihypertensive activity

Rats are anaesthetised with pentobarbitone and catheters are introduced into the right external jugular vein and the left carotid artery. The arterial catheter is coupled to a transducer for measuring blood pressure and the compound under test is administered intravenously at a dose of 10 or 30 μg. per kg. bodyweight. The fall in diastolic blood pressure from its initial value, 15 minutes after administration of the compound, is recorded in mm. Hg.

Sedative activity (a) Agility

Groups of 6 mice are dosed orally with the compound under test and after 1 hour attempts are made to allow each mouse to stand for 20 seconds on a rod 40 cm. long and 1 cm. in diameter, each mouse being placed at least a tail length from the end of the rod. 4 Attempts are allowed for each mouse, and the number of successful attempts is recorded. The maximum score for the group is therefore 24. A compound is regarded as active if the score is less than or equal to 13. Animals are dosed at 0.1, 0.3, 1, 3, 10 and 30 mg. per kg. bodyweight and the minimum active dose is recorded.

(b) Locomotor activity

Groups of 6 mice are dosed orally with the compound under test and after 30 minutes are placed individually in cages provided with a central horizontal scanning photobeam. The number of beam interruptions in the first 45 minutes is recorded, and the mean percentage inhibition of movement relative to the mean movement of undosed control animals is calculated. A compound is considered active in the amount of movement is reduced by more than one third compared with that of the control animals. Animals are dosed at 0.1, 0.3, 1, 3, 10 and 30 mg. per kg. bodyweight and the minimum active dose is recorded.

| Ar | Reduction of blood pressure (mm. Hg.) at doses 10 μg./kg. | 30 μg./kg. | Minimum active sedative dose (mg./kg.) Agility | Locomotor activity |
|---|---|---|---|---|
| 2,6-dichlorophenyl | 28 | 58 | 3 | 1 |
| 2-chloro-6-fluorophenyl | 30 | 35 | 30 | 3 |
| 2-chloro-6-methylphenyl | 26 | | 3 | 3 |
| 2,6-dimethylphenyl | 15 | | 1 | 3 |
| 2,6-dichloro-3-methylphenyl | 13 | 33 | 1 | 1 |
| 2-methylnaphth-1-yl | 19 | 35 | 30 | 3 |
| (indane-1)spiro-6- | | 31 | 1 | 1 |
| Clonidine | 41 | 45 | 0.3 | 0.1 |

The compound 6-(2,6-dichlorophenyl)-2,3,6,7-tetrahydro-5H-pyrrolo[1,2-a]imidazole, when administered orally to a dog for five days at a dose of 250 μg. per kg. bodyweight every 4 hours, reduced the systolic blood pressure from 152 mm. to 125 mm. Hg. and the diastolic blood pressure from 103 mm. to 75 mm. Hg.

Under similar conditions the compound 6-(2-chloro-6-fluorophenyl)-2,3,6,7-tetrahydro-5H-pyrrolo[1,2-a]imidazole reduced the systolic blood pressure from 149 mm. to 115 mm. Hg. and the diastolic blood pressure from 109 mm. to 65 mm. Hg. A similar experiment with clonidine had to be terminated after 24 hours because the dog became heavily sedated. In both cases involving compounds of the invention blood pressures reverted to their original levels three days after withdrawal of the medicament.

The compound of the invention may be administered to warm-blooded animals, including man, in the form of a pharmaceutical composition comprising as active ingredient at least one compound of the invention, or an acid-additon salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the compound of the invention, one or more drugs selected from vasodilators, for example glyceryl trinitrate, pentaerythritol tetranitrate and isosorbide dinitrate; diuretics, for example chlorothiazide; other hypotensive agents, for example reserpine, bethanidine and guanethidine; and β-adrenergic blocking agents, for example propranolol.

When used for the treatment of hypertension in man, it is expected that the compound of the invention would be given to man at a total oral dose of between 0.1 mg. and 5 mg. daily, at doses spaced at 6-8 hourly intervals, or at an intravenous dose of between 0.01 mg. and 1 mg.

Preferred oral dosage forms are tablets or capsules containing between 0.1 mg. and 1 mg. of active ingredient. Preferred intravenous dosage forms are sterile aqueous solutions of the compound of the invention or of a non-toxic acid-addition salt thereof, containing between 0.05% and 0.1% w/v of active ingredient.

The invention is illustrated but not limited by the following Examples:

EXAMPLE 1

A solution of 2-β-bromoethylimino-4-(2,6-dichlorophenyl)pyrrolidine hydrobromide (1.8 g.) in water (50 ml.) is added dropwise at laboratory temperature to a stirred solution of potassium carbonate (1.38 g.) in water (50 ml.), and the mixture is stirred for 15 minutes after addition is complete and then extracted three times with ethyl acetate (50 ml. each time). The combined extracts are dried and evaporated to dryness and the residue is dissolved in ethyl acetate (15 ml.). An excess of ethereal hydrogen chloride solution is added and the mixture is filtered. The solid residue is crystallised from a mixture of ethanol and ethyl acetate and there is thus obtained 6-(2,6-dichlorophenyl)-2,3,6,7-tetrahydro-5H-pyrrolo[1,2-a]imidazole hydrochloride, m.p. 287°–288° C.

The pyrrolidine derivative used as starting material may be obtained as follows:

2-Bromoethylamine hydrobromide (4.1 g.) is added to a solution of 4-(2,6-dichlorophenyl)-2-ethoxy-1-pyrroline (5.2 g.) in ethanol (50 ml.) and the mixture is heated under reflux for 10 hours and then evaporated to dryness. The residue is crystallised from ethanol and there is thus obtained 2-β-bromoethylimino-4-(2,6-dichlorophenyl)pyrrolidine hydrobromide, m.p. 244°–246° C.

EXAMPLE 2

The process described in Example 1 is repeated except that 2-β-bromoethylimino-4-(2,6-dimethylphenyl)-pyrrolidine hydrobromide (m.p. 208°–211° C., prepared by a similar process to that described in the second part of Example 1 from 4-(2,6-dimethylphenyl)-2-ethoxy-1-pyrroline) is used as starting material. There is thus obtained 6-(2,6-dimethylphenyl)-2,3,6,7-tetrahydro-5H-pyrrolo[1,2-a]imidazole hydrochloride, m.p. 226°–227° C.

EXAMPLE 3

The process described in Example 1 is repeated except that the appropriate 2-β-bromoethylimino-4-arylpyrrolidine hydrobromide is used as starting material. There are thus obtained the compounds described in the following table:

| 6-aryl-2,3,6,7-tetrahydro-5H-pyrrolo[1,2-a]-imidazole hydrobromides | | |
|---|---|---|
| 6-aryl group | m.p. (° C.) | crystallisation solvent |
| 2-chlorophenyl | 169–171 | isopropanol/ethyl acetate |
| 2-bromo-6-chlorophenyl | 308–310 (decomp.) | ethanol/isopropanol |
| 2-chloro-6-trifluoromethylphenyl | 305 (decomp.) | ethanol/ethyl acetate |
| 2,4,6-trichlorophenyl | 273–274 | isopropanol/ether |
| 2-chloro-6-methoxyphenyl | 204–206 | isopropanol |
| 2-fluoro-6-trifluoromethylphenyl | 223–226 | isopropanol |
| 2,6-dichloro-3-nitrophenyl | 290–292 | ethanol |
| 2,6-dichloro-3-methylphenyl | 280–281 | isopropanol |
| 2,6-dichloro-3-methoxyphenyl | 237–238 | isopropanol |
| 2-methylnaphth-1-yl | 276–277 | ethanol/isopropanol |
| 2-chloronaphth-1-yl | 288–290 | ethanol |
| 4-bromo-2,5-dimethylthien-3-yl | 267–268 | isopropanol |
| 2,5-dimethylthien-3-yl | 234–235 | isopropanol/ethyl acetate |

The various 2-β-bromoethylimino-4-arylpyrrolidine hydrobromides used as starting materials may be obtained by a similar process to that described in the second part of Example 1 from te appropriate 4-aryl-2-ethoxy-1-pyrroline derivatives, and these compounds are described in the following table:

| 2-β-bromoethylimino-4-arylpyrrolidine hydrobromides | | |
|---|---|---|
| 4-aryl group | m.p.(° C.) | cyrstallisation solvent |
| 2-chlorophenyl | 184–186 | ethanol |
| 2-bromo-6-chlorophenyl | 246–248 (decomp.) | ethanol |
| 2-chloro-6-trifluoromethylphenyl | 243–245 (decomp.) | isopropanol/ethyl acetate |
| 2,4,6-trichlorophenyl | 243–245 | isopropanol/ethanol |
| 2-chloro-6-methoxyphenyl | 213–215 | isopropanol |
| 2-fluoro-6-trifluoromethylphenyl | 167–172 | — |
| 2,6-dichloro-3-nitrophenyl | 244–246 | ethanol |
| 2,6-dichloro-3-methylphenyl | 248–250 | ethanol |
| 2,6-dichloro-3-methoxyphenyl | 209–211 | isopropanol |
| 2-methylnaphth-1-yl | 224–226 | ethanol |

-continued

| 2-β-bromoethylimino-4-arylpyrrolidine hydrobromides | | |
|---|---|---|
| 4-aryl group | m.p. (° C.) | cyrstallisation solvent |
| 2-chloronaphth-1-yl | 237–239 | ethanol |
| 4-bromo-2,5-dimethylthien-3-yl | 241–242 (decomp.) | ethanol |
| 2,5-dimethylthien-3-yl | 220–222 | ethanol |

EXAMPLE 4

A stirred mixture of 2-β-bromoethylamino-4-(2,6-dichlorophenyl)-1-pyrroline hydrobromide (46.35 g.), anhydrous sodium bicarbonate (9.3 g.) and dry isopropanol (350 ml.) is heated under reflux for 4 hours with exclusion of moisture, the hot mixture is filtered and the solid residue is stirred and heated under reflux with dry isopropanol (350 ml.) for 1 hour. The hot mixture is filtered and the combined isopropanol filtrates are evaporated to dryness under reduced pressure. The residue is dissolved in boiling ethanol (200 ml.) and the solution is concentrated to 125 ml. and allowed to cool. The mixture is filtered and there is thus obtained as solid residue 6-(2,6-dichlorophenyl)-2,3,6,7-tetrahydro-5H-pyrrolo[1,2-a]imidazole hydrobromide, m.p. 297°–299° C.

The 2-β-bromoethylamino-4-(2,6-dichlorophenyl)-1-pyrroline hydrobromide used as starting material may be obtained from 2,6-dichlorobenzaldehyde as follows:

Nitromethane (9.15 g.) is added to a stirred solution of 2,6-dichlorobenzaldehyde (17.6 g.) in ethanol (100 ml.) which is maintained at −10° C., and a solution of potassium hydroxide (11.2 g.) in a mixture of water (20 ml.) and ethanol (30 ml.) is added during 30 minutes to the cooled solution. The mixture is stirred at −10° C. for a further 2 hours, 50% v/v aqueous acetic acid (25 ml.) is added and the mixture is evaporated to dryness under reduced pressure at a temperature below 35° C. The residue is shaken with ether (100 ml.) and and water (100 ml.) and the ethereal solution is separated, dried and evaporated to dryness.

A mixture of the 1-(2,6-dichlorophenyl)-2-nitroethanol thus obtained (9.45 g.), anhydrous sodium acetate (13.2 g.) and acetic anhydride (61.5 g.) is heated under reflux for 5 minutes and then poured into a stirred mixture of ice and water (400 ml.). The mixture is filtered and the solid residue is washed with water, dried and crystallised from ethanol. There is thus obtained 1-(2,6-dichlorophenyl)-2-nitroethylene, m.p. 62°–63° C.

Dimethyl malonate (42 g.) and 1-(2,6-dichlorophenyl)-2-nitroethylene (66 g.) are added to a stirred solution of sodium (0.3 g.) in dry methanol (200 ml.) and the mixture is stirred at laboratory temperature for 3 hours and then made slightly acidic with ethereal hydrogen chloride solution. The mixture is kept at 0° C. for 24 hours and then filtered, and the solid residue is crystallised from methanol. There is thus obtained methyl 3-(2,6-dichlorophenyl)-2-methoxycarbonyl-4-nitrobutyrate, m.p. 87°–89° C.

A solution of the above ester (95.5 g.) in methanol (1 liter) is shaken with hydrogen in the presence of a Raney nickel catalyst (15 g.) at 50° C. and a pressure of 10 atmospheres until the theoretical amount of hydrogen required for reduction of the nitro group has been absorbed. The mixture is warmed to dissolve precipitated organic solid and then filtered, and the filtrate is evaporated to dryness under reduced pressure. The residue is triturated with ice-cold methanol, the mixture is filtered and the solid residue is crystallised from methanol. There is thus obtained 4-(2,6-dichlorophenyl)-3-methoxycarbonylpyrrolidin-2-one, m.p. 175°–177° C.

A stirred mixture of the above pyrrolidinone (51.1 g.), potassium hydroxide (20 g.) and water (200 ml.) is heated at 40° C. for 2 hours, when solution is substantially complete, and the mixture is filtered. The filtrate is acidified with concentrated aqueous hydrochloric acid and the mixture is filtered. The solid residue, which consists of 4-(2,6-dichlorophenyl)-2-oxopyrrolidine-3-carboxylic acid, is washed with water, dried and ground to a fine powder. The powder is heated at 200° C. in a stream of dry nitrogen until gas effervescence from the molten material ceases. The product is cooled and dissolved in boiling ethyl acetate (700 ml.), the hot solution is filtered and the filtrate is concentrated by evaporation until crystallisation begins. The mixture is cooled and filtered, and the solid product is crystallised from ethyl acetate. There is thus obtained 4-(2,6-dichlorophenyl)-pyrrolidin-2-one, m.p. 164°–166° C.

A freshly prepared solution of triethyloxonium fluoroborate in dichloromethane (50 ml., approximately 0.5g./ml.) is added during 15 minutes through a syringe to a stirred solution of 4-(2,6-dichlorophenyl)pyrrolidin-2-one (30 g.) in dichloromethane (200 ml.) which is maintained under nitrogen, and the mixture is kept at laboratory temperature for 18 hours. 50% W/v aqueous potassium carbonate solution (50 ml.) is added and the mixture is stirred for 30 minutes and then filtered. The dichloromethane solution is separated from the aqueous layer, dried and evaporated to dryness under reduced pressure. The residual oil consists of 4-(2,6-dichlorophenyl)-2-ethoxy-1-pyrroline and is used without further purification.

β-Bromoethylamine hydrobromide (26.7 g.) is added to a stirred solution of the above compound (36 g.) in dry ethanol (150 ml.) and the mixture is kept at laboratory temperature for 18 hours and then cooled and filtered. The filtrate is concentrated to 50 ml. by evaporation, ether (50 ml.) is added and the mixture is filtered. The combined solid residues are crystallised from ethanol and there is thus obtained 2-β-bromoethylamino-4-(2,6-dichlorophenyl)-1-pyrroline hydrobromide, m.p. 244°–246° C.

EXAMPLE 5

The process described in Example 4 is repeated except that the appropriate 2-β-bromoethylamino-4-aryl-1-pyrroline hydrobromide is used as starting material. There are thus obtained the compounds described in the following table:

| 6-aryl-2,3,6,7-tetrahydro-5H-pyrrolo-[1,2-a]imidazole hydrobromides | | |
|---|---|---|
| 6-aryl group | m.p.(° C.) | crystallisation solvent |
| 2-chloro-6-methylphenyl | 280–282 | ethanol |
| 2-chloro-6-fluorophenyl | 211–213 | ethanol/ethyl acetate |

The various 2-β-bromoethylamino-4-aryl-1-pyrroline hydrobromides used as starting materials may be obtained by a similar process to that described in the second part of Example 4, and these compounds are described in the following table:

| 2-β-bromoethylamino-4-aryl-1-pyrroline hydrobromides | | |
|---|---|---|
| 4-aryl group | m.p.(° C.) | crystallisation solvent |
| 2-chloro-6-methyl-phenyl | 247–250 | ethanol |
| 2-chloro-6-fluoro-phenyl | 214–216 | ethanol |

The various intermediates used in the preparation of the 2-iminopyrrolidine or 2-amino-1-pyrroline starting materials used in Examples 1 to 5 may be obtained by similar processes to those described in the later parts of Example 4. Those compounds which have been characterised are described in the following table:

| | Melting Point (° C.) | | | |
|---|---|---|---|---|
| Aryl | 1-Aryl-2-nitro ethylene | Methyl 3-aryl-2-methoxycarbonyl-4-nitrobutyrate | 4-Aryl-3-methoxycarbonyl-pyrrolidin-2-one | 4-Aryl-pyrrolidin-2-one |
| 2,6-dimethylphenyl | 49–51 | (oil) | 183–185 | 175–177 |
| 2-chloro-6-methylphenyl | (b.p. 118–120° C./35 mm.) | 62–64 | 190–192 | 164–165 |
| 2-chlorophenyl | 46–48 | (oil) | 105–106 | 117–118 |
| 2-chloro-6-fluorophenyl | 64–65 | 72–74 | 150–152 | 115–118 |
| 2-bromo-6-chlorophenyl | 74–76 | 75–77 | 194–198 | 155–157 |
| 2-chloro-6-trifluoromethyl-phenyl | (oil) | 92–93 | 177–180 | 151–152 |
| 2,4,6-trichlorophenyl | 101–103 | 100–101 | 180–182 | 170.5–171.5 |
| 2-chloro-6-methoxyphenyl | 69–72 | (oil) | 113–115 | 136–137 |
| 2-fluoro-6-trifluoromethyl-phenyl | 61–63 | 86–90 | 134–136 | 108–109 |
| 2,6-dichloro-3-methylphenyl | 51–52 | 120–123 | 152–154 | 185–187 |
| 2,6-dichloro-3-methoxy-phenyl | 113–115 | 110–112 | 172–174 | 185–187 |
| 2,6-dichloro-3-nitro-phenyl | — | — | — | 208–210+ |
| 2-methylnaphth-1-yl | 81–83 | (oil) | 166–167 | 145–146 |
| 2-chloronaphth-1-yl | 88–90 | 116–117 | 157–162 | 148–150 |
| 2,5-dimethylthien-3-yl | 64–68 | 70–71 | 141–143 | 94–96 |
| 4-bromo-2,5-dimethylthien-3-yl | — | — | — | 140–142* |

+Prepared from unnitrated compound by reaction with nitric/sulphuric acids at 5–10° C.
*Prepared from unbrominated compound by reaction with bromine in carbon tetrachloride at 0–5° C.

Most of the benzaldehyde derivatives or analogues used as initial starting materials are known compounds. Those which are novel may be obtained by metallation and formylation of the appropriate benzene derivative or analogue by a similar process to that described by Roe et alia, Journal of Medicinal Chemistry, 1968, 11, 814, and are characterised as follows:

| | Ar—CHO | |
|---|---|---|
| Ar | m.p. (° C.) | b.p. (° C.) |
| 2-chloro-6-trifluoromethylphenyl | | 46–52°/1 mm. Hg. |
| 2,6-dichloro-3-methylphenyl | 102–103 | |
| 2-chloronaphth-1-yl | 76–78 | |
| 2-fluoro-6-trifluoromethylphenyl | | 61–67°/10 mm. Hg. |
| 2,5-dimethylthien-3-yl | | 97–99°/11 mm. Hg. |

EXAMPLE 6

The process described in Example 1 is repeated except that (indane-1)spiro[4-(2-β-bromoethylimino)pyrrolidine] hydrobromide is used as starting material. There is thus obtained (indane-1)spiro[6-(2,3,6,7-tetrahydro-5H-pyrrolo[1,2-a]imidazole)] hydrobromide, m.p. 205°–207° C. after crystallisation from a mixture of isopropanol and diethyl ether.

The (idane-1)spiro[4-(2-β-bromoethylimino)pyrolidine] hydrobromide used as starting material may be obtained as follows:

A 15% w/v solution of n-butyl-lithoum in hexane (5 ml.) is added to a stirred solution of hexamethyldisilazane (1.77 g.) in dry tetrahydrofuran (20 ml.) which is maintained at 0° C. under an atmosphere of nitrogen. After 10 minutes a solution of 1-cyanoindane (1.43 g.) in dry tetrahydrofuran (5 ml.) is added during 5 minutes, and after a further 15 minutes a solution of ethyl bromoacetate (1.7 g.) in dry tetrahydrofuran (5 ml.) is added. The mixture is allowed to warm up to laboratory temperature, kept thus for 1 hour and saturated aqueous sodium chloride solution (25 ml.) is added. The organic layer is separated, dried and evaporated to dryness and the residue is distilled, the fraction having boiling point 120°–130° C./0.1 mm. Hg. being collected. A solution of this product, which consists of ethyl 1-cyanoindan-1-ylacetate (8 g.) in ethanol (50 ml.) is shaken with hydrogen in the presence of a Raney nickel catalyst (1 g.) at laboratory temperature and atmospheric pressure for 36 hours and then filtered. The filtrate is evaporated to dryness and the residue is stirred with cyclohexane (25 ml.) for 3 days and then filtered. The solid residue is crystallised from a mixture of cyclohexane and toluene and then from ethanol and there is thus obtained (indane-1)spiro[4-(2-oxopyrrolidine)], m.p. 165°–167° C.

The compound is converted into the corresponding 2-ethoxy-1-pyrroline derivative by a similar process to that described in the penultimate paragraph of Example 4, and the ethoxy compound is converted into the desired product by a similar process to that described in the second part of Example 1. There is thus obtained (indane-1)spiro[4-(2-β-bromoethylimino)-pyrrolidine] hydrobromide, m.p. 212°–214° C. after crystallisation from ethanol.

EXAMPLE 7

The process described in Example 1 is repeated except that the appropriate 2-β-bromoethylimino-4-(2,6-dichlorophenyl)-methylpyrrolidine hydrobromide is used as starting material. There are thus obtained the compounds described in the following table:

| 6-(2,6-dichlorophenyl)methyl-2,3,6,7-tetra-hydro-5H-pyrrolo[1,2-a]imidazole hydrobromides | | |
|---|---|---|
| position of methyl group | m.p. (° C.) | crystallisation solvent |
| 7- | 223–225 | methanol/ether |
| 6- | 266–268 | isopropanol |
| 5- (first isomer) | 210–211.5 | isopropanol/ethyl acetate |
| 5- (second isomer) | 259–260 | isopropanol/ethyl acetate |

The various 2-β-bromoethylimino-4-(2,6-dichlorophenyl)-methylpyrrolidine hydrobromides used as starting materials may be obtained by a similar process to that described in the second part of Example 1 from the appropriate 4-(2,6-dichlorophenyl)-2-ethoxy-methyl-1-pyrroline derivatives, and these compounds are described in the following table:

| position of methyl group | m.p. (° C.) | crystallisation solvent |
|---|---|---|
| 3- | (oil) | — |
| 4- | 243–245 | ethanol |
| 5- (first isomer) | 194–197 | ethanol |
| 5- (second isomer) | 226–228 | ethanol |

The 2-ethoxy-1-pyrroline derivatives may be obtained from the corresponding 4-(2,6-dichlorophenyl)-methylpyrrolidin-2-one derivatives by a similar process to that described in the penultimate paragraph of Example 4, and the various pyrrolidin-2-one derivatives themselves may be obtained as follows:

4-(2,6-Dichlorophenyl)-4-methylpyrrolidin-2-one

A 2M- solution of dimsyl sodium in dry dimethylsulphoxide (50 ml.) is added to a stirred solution of 2,6-dichlorobenzyl cyanide (18.6 g.) in dry dimethylsulphoxide (200 ml.) which is maintained at a temperature of 25° C. under an atmosphere of nitrogen. After 15 minutes methyl iodide (14.2 g.) is added dropwise and the mixture is left at laboratory temperature for 90 minutes and then poured into ice-water (500 ml.). The mixture is extracted three times with ethyl acetate (100 ml. each time) and the combined extracts are washed twice with 5% aqueous sodium bicarbonate solution (100 ml. each time), twice with water (100 ml. each time) and once with saturated brine (100 ml.), dried and evaporated to dryness. The residue is distilled and there is thus obtained α-(2,6-dichlorophenyl)ethylcyanide, b.p. 96°–98° C./0.5 mm. Hg.

A solution of the above product (16.8 g.) in dry tetrahydrofuran (25 ml.) is added dropwise to a stirred solution of lithium hexamethyldisilazane [prepared as described in Example 6 from a 12% w/v solution of n-butyl lithium (49 ml.) and hexamethyldisilazane (14.9 g.)] in dry tetrahydrofuran (50 ml.) which is maintained at −70° C. under an atmosphere of nitrogen, and the mixture is kept at that temperature for 1 hour. Ethyl bromoacetate (14 g.) is added dropwise during 5 minutes and the mixture is kept at −70° C. for 1 hour, allowed to warm up to −20° C. and poured into ice-water (200 ml.). The mixture is extracted with ether and the ethereal extract is dried and evaporated to dryness. The residue is purified by chromatography on a silica gel column eluted with a 1:9 v/v mixture of ethyl acetate and toluene. There is thus obtained ethyl 3-(2,6-dichlorophenyl)-3-cyanobutyrate, m.p. 55°–57° C.

A solution of the above compound (10 g.) in ethanol (150 ml.) is shaken with hydrogen in the presence of a Raney nickel catalyst (2 g.) at 75° C. and a pressure of 10 atmospheres until 2 equivalents of hydrogen have been absorbed. The mixture is filtered, the filtrate is evaporated to dryness and the residue is crystallised from ethyl acetate. There is thus obtained 4-(2,6-dichlorophenyl)-4-methylpyrrolidin-2-one, m.p. 154°–158° C.

4-(2,6-Dichlorophenyl)-3-methylpyrrolidin-2-one 4-(2,6-Dichlorophenyl)-3-methoxycarbonylpyrrolidin-2-one (2.88 g.; Example 4) is added to a suspension of an 80% dispersion of sodium hydride in mineral oil (0.32 g.) in dry tetrahydrofuran (50 ml.). After evolution of hydrogen ceases methyl iodide (1.42 g.) is added and the mixture is stirred and heated at 40° C. under an atmosphere of nitrogen for 1 hour and then evaporated to dryness. Water (100 ml.) is added to the residue, the mixture is filtered and the solid residue is crystallised from methanol. There is thus obtained 4-(2,6-dichlorophenyl)-3-methoxycarbonyl-3-methylpyrrolidin-2-one, m.p. 234°–236° C.

A mixture of the above compound (1.8 g.), ethanol (40 ml.), water (10 ml.) and potassium hydroxide (2 g.) is stirred and heated under reflux for 4 hours and cooled, and water (150 ml.) is added. The mixture is acidified with aqueous 2N-hydrochloric acid and then filtered, and the the solid residue is dried, ground to a fine powder and heated at 200° C. in a stream of nitrogen until gas effervescence from the molten material ceases. The product is cooled and crystallised from ethyl acetate and there is thus obtained 4-(2,6-dichlorophenyl)-3-methylpyrrolidin-2-one, m.p. 175°–177° C.

4-(2,6-Dichlorophenyl)-5-methylpyrrolidin-2-one 1-(2,6-Dichlorophenyl)-2-nitropropylene (m.p. 49°–50° C., b.p. 90°–102° C./0.33 mm. Hg.) is prepared from nitroethane and 2,6-dichlorobenzaldehyde by a similar process to that described in the second and third parts of Example 4. This compound is reacted with dimethyl malonate and the product hydrogenated by a similar process to that described in the fourth and fifth parts of Example 4, and the 4-(2,6-dichlorophenyl)-3-methoxycarbonyl-5-methylpyrrolidin-2-one thus obtained is separated into two geometrical isomers thereof by repeated chromatography on a silica gel column, using a 2:1 v/v mixture of toluene and ethyl acetate as eluant. The two isomers have m.p. 157°–158° C. (first isomer) and 143°–144° C. (second isomer). These two esters are separately hydrolysed and decarboxylated by a similar process to that described in the sixth part of Example 4, and there are thus obtained a first isomer, m.p. 182°–184° C., and a second isomer, m.p. 173.5°–175° C., of 4-(2,6-dichlorophenyl)-5-methylpyrrolidin-2-one, the isomers differing by cis- and trans-relationship of the 4-(2,6-dichlorophenyl)- and 5-methyl-subsitutents.

EXAMPLE 8

The process described in Example 4 is repeated except that there are separately used as starting materials the (+)- and (−)- isomers of 2-β-bromoethylamino-4-(2,6-dichlorophenyl)-1-pyrroline hydrobromide. There are thus obtained (−)-6-(2,6-dichlorophenyl)-2,3,6,7-tetrahydro-5H-pyrrolo[1,2-a]-imidazole hydrobromide, m.p. 304° C. (with decomposition), $[\alpha]_D^{25} = -32.7°(H_2O, c=0.11)$ and (+)-6-(2,6-dichlorophenyl)-2,3,6,7-tetrahydro-5H-pyrrolo[1,2-a]imidazole hydrobromide, m.p. 304° C. (with decomposition), $[\alpha]_D^{25} = +31.8°(H_2O, c=0.11)$.

The optically-active starting materials may be obtained as described in the later parts of Example 4 except that the 4-(2,6-dichlorophenyl)-2-oxypyrrolidine-3-carboxylic acid (sixth part of Example 4) is crystallised from aqueous ethanol, the product obtained then being a pure geometrical isomer at the 3- and 4-positions. d-(+)-α-Phenylethylamine (8.5 g.) is added quickly to a solution of this acid (18 g.) in hot ethanol (350 ml.) and the mixture is kept at laboratory temperature for 2 days and then filtered. The solid product is crystallised from ethanol and there is thus obtained one salt of the acid and the amine, m.p. 186°–187° C. (with decomp.) The mother liquors from the original crystallisation are concentrated to half volume and again kept at laboratory temperature for 2 days and then filtered. The solid product is crystallised from ethanol and there is thus obtained a second salt of the acid and the amine, m.p. 170°–172° C. (with decomposition).

Each salt (7 g.) is separately dissolved in warm water (600 ml.) and the solution is acidified with aqueous 2N-hydrochloric acid and filtered. The solid free acid is then decarboxylated as described in the sixth part of Example 4. There are thus obtained the two optical isiomers of 4-(2,6-dichlorophenyl)pyrrolidin-2-one, the (−) isomer (obtained from the higher-melting salt) having $[α]_D^{25} = -3.6°$(chloroform, c=0.05) and the (+) isomer (obtained from the lower-melting salt) having $[α]_D^{25} = +3.5°$ (chloroform, c=0.046), both isomers having m.p. 153°–154° C. after crystallisation from ethyl acetate.

Each isomer is separately converted to the 2-ethoxy-1-pyrroline derivative and then to the 2-β-bromoethylamino-1-pyrroline hydrobromide as described in the last two parts of Example 4.

EXAMPLE 9

A mixture of 4-(2,6-dichlorophenyl)pyrrolidin-2-one (1.15 g.) and ethanolamine hydrobromide (0.71 g.) is heated under an atmosphere of nitrogen for 12 hours at 180°–190° C., cooled and shaken with chloroform and aqueous 2N-hydrochloric acid. The aqueous layer is separated, basified with aqueous 2N-sodium hydroxide solution and extracted with chloroform. The extract is dried and evaporated to dryness and the residue is chromatographed on silica gel plates (Kieselgel GF$_{254}$) using a 2% v/v solution of aqueous ammonium hydroxide solution (s.g. 0.89) in methanol as eluant. The appropriate fraction is isolated, dissolved in ethanol and treated with an excess of ethereal hydrogen bromide solution. The mixture is evaporated to dryness and the residue is crystallised from isopropanol. There is thus obtained 6-(2,6-dichlorophenyl)-2,3,6,7-tetrahydro-5H-pyrrolo[1,2-a]imidazole hydrobromide, m.p. 297°–299° C.

EXAMPLE 10

A mixture of 1-β-aminoethyl-4-(2,6-dichlorophenyl)-pyrrolidin-2-one (0.7 g.) and phosphorus oxychloride (10 ml.) is stirred at laboratory temperature for 18 hours and the excess of phosphorus oxychloride is removed by distillation. Triethylamine (0.5 ml.) is added to a solution of the residue in ethanol (10 ml.) and the mixture is heated under reflux for 30 minutes and then evaporated to dryness. The residue is shaken with chloroform and aqueous 2N-sodium hydroxide solution and the chloroform layer is separated, dried and evaporated to dryness. The residue is dissolved in ethanol and an excess of ethereal hydrogen bromide solution is added. The mixture is evaporated to dryness and the hydrobromide salt thus obtained is crystallised from isopropanol. There is thus obtained 6-(2,6-dichlorophenyl)-2,3,6,7-tetrahydro-5H-pyrrolo[1,2-a]imidazole hydrobromide, m.p. 297°–299° C.

The 1-β-aminoethyl-4-(2,6-dichlorophenyl)pyrrolidin-2-one used as starting material may be obtained as follows:

Methanol (10 ml.) is added to a freshly prepared, stirred suspension of sodium (0.575 g.) in toluene (75 ml.) which is kept under an atmosphere of nitrogen and the excess of methanol is removed by azeotropic distillation. 4-(2,6-Dichlorophenyl)pyrrolidin-2-one (5.75 g.) is added and azeotropic distillation is continued for a further 30 minutes. The mixture is stirred and cooled to laboratory temperature, chloroacetonitrile (2.08 g.) is added dropwise during 10 minutes, and the mixture is stirred at laboratory temperature for 18 hours. Water (75 ml.) is added, and sufficient ethyl acetate is added to form two clear layers. The organic layer is separated, washed with water, dried and evaporated to dryness under reduced pressure. The residue is dissolved in methanol (100 ml.) and the solution is shaken with hydrogen in the presence of a Raney nickel catalyst (1.0 g.) at laboratory temperature and atmospheric pressure until uptake of hydrogen ceases. The mixture is filtered the filtrate is evaporated to dryness and the residue is dissolved in chloroform (100 ml.). The solution is extracted three times with aqueous 2N-hydrochloric acid (25 ml. each time) and the combined extracts are basified with aqueous 2N-sodium hydroxide solution. The mixture is extracted twice with chloroform (50 ml. each time) and the combined extracts are dried and evaporated to dryness. The residue is crystallised from a mixture of ethanol and ethyl acetate and there is thus obtained 1-β-aminoethyl-4-(2,6-dichlorophenyl)pyrrolidin-2-one, m.p. 128°–130° C.

EXAMPLE 11

A mixture of 2-(γ-chloro-β-2,6-dichlorophenylpropyl)-1-imidazoline hydrobromide (0.4 g.), anhydrous sodium bicarbonate (0.1 g.) and isopropanol (20 ml.) is heated under reflux for 4 hours and then evaporated to dryness. The residue is shaken with chloroform (10 ml.) and aqueous 2N-sodium hydroxide solution and the aqueous layer is separated and extracted three times with chloroform (10 ml. each time). The combined chloroform solutions are washed with water (10 ml.), dried and evaporated to dryness and the residue is dissolved in ethanol. An excess of ethereal hydrogen bromide solution is added, the mixture is evaporated to dryness and the solid residue is crystallised from ethanol. There is thus obtained 6-(2,6-dichlorophenyl)-2,3,6,7-tetrahydro-5H-pyrrolo[1,2-a]imidazole hydrobromide, m.p. 297°–299° C.

The 2-(γ-chloro-β-2,6-dichlorophenylpropyl)-1-imidazoline hydrobromide used as starting material may be obtained as follows:

A mixture of 4-(2,6-dichlorophenyl)pyrrolidin-2-one (1.0 g.), concentrated aqueous hydrochloride acid (10 ml.) and water (10 ml.) is heated under reflux for 8 hours and then evaporated to dryness under reduced pressure. The residue is crystallised from isopropanol and there is thus obtained 4-amino-3-(2,6-dichlorophenyl)butyric acid hydrochloride, m.p. 105°–115° C. (with decomposition).

A mixture of the above compound (20 g.), water (150 ml.) and glacial acetic acid (50 ml.) is stirred and cooled to −12° C. and a solution of sodium nitrite (12 g.) in water (30 ml.) is added dropwise at such a rate that the temperature of the mixture does not rise above −10° C. The mixture is kept at −10° C. for a further 30 minutes, allowed to reach laboratory temperature during a further 1 hour, and is then extracted four times with ethyl acetate (75 ml. each time). The combined extracts are washed with dilute aqueous ammonium hydroxide solution, then with aqueous 2N-hydrochloric acid and finally with water, dried and evaporated to dryness. The residue consists of 4-(2,6-dichlorophenyl)tetrahydrofuran-2-one and is used without further purification.

A mixture of the above compound (4 g.) and ethylenediamine (15 ml.) is heated at 95°–100° C. for 15 minutes and then evaporated to dryness under reduced pressure. The residue is stirred with cyclohexane (50 ml.) until it solidifies, the cyclohexane is decanted off and the solid residue is dissolved in boiling ethyl acetate (300 ml.). The solution is filtered and the filtrate is concentrated to 130 ml. by distillation and then cooled. The mixture is filtered and there is thus obtained as solid residue N-β-aminoethyl-3-(2,6-dichlorophenyl)-4-hydroxybutyramide, m.p. 127°–129° C.

A mixture of the above compound (1.0 g.) and phosphorus oxychloride (20 ml.) is heated at 95°–100° C. for 40 minutes and then evaporated to dryness under reduced pressure, finally at 40° C. under high vacuum to remove last traces of phosphorus oxychloride. The residue is dissolved in ethanol (50 ml.), sufficient triethylamine is added to neutralise the solution and the mixture is kept at laboratory temperature for 18 hours and then partitioned between chloroform and aqueous 2N-sodium hydroxide solution. The aqueous layer is separated and extracted three times with chloroform and the combined chloroform solutions are dried and evaporated to dryness under reduced pressure, finally at high vacuum to remove last traces of triethylamine. The residue is dissolved in ethanol, an excess of ethereal hydrogen bromide solution is added and the mixture is evaporated to dryness. The solid residue is crystallised from a mixture of ethanol and ether and there is thus obtained 2-(γ-chloro-β-2,6-dichlorophenylpropyl)-1-imidazoline hydrobromide, m.p. 233°–236° C.

EXAMPLE 12

A 1.6M-solution of n-butyl-lithium in hexane (7.15 ml.) is added to a solution of di-isopropylamine (1.52 ml.) in dry tetrahydrofuran (15 ml.) which is maintained at −40° C. under an atmosphere of nitrogen. After 20 minutes the mixture is cooled to −60° C. and a solution of 3-(β-chloro-β-2,6-dichlorophenylethyl)-2-methyl-1-imidazoline (2.91 g.) in tetrahydrofuran (10 ml.) is added. The mixture is allowed to warm up to −10° C., kept at this temperature for 2 hours and then poured onto ice (200 g.). The mixture is extracted with ether and the ethereal extract is dried and treated with saturated ethereal oxalic acid solution. The mixture is filtered and the solid product is crystalised from a mixture of ethanol and ethyl acetate. There is thus obtained 6-(2,6-dichlorophenyl)-2,3,6,7-tetrahydro-5H-pyrrolo[1,2-a]imidazole hydrogen oxalate, m.p. 199°–200° C.

The 3-(β-chloro-β-2,6-dichlorophenylethyl)-2-methyl-1-imidazoline used as starting material may be obtained as follows:

Trimethylsulphoxonium iodide (150 g.) is added to a stirred suspension of 65% w/w sodium hydride in mineral oil (25 g.) in dry dimethylsulphoxide (375 ml.) under an atmosphere of nitrogen. After 1 hour a solution of 2,6-dichlorobenzaldehyde (105 g.) in dry dimethylsulphoxide (450 ml.) is added at such a rate that the temperature does not exceed 18° C. The mixture is stirred for a further 30 minutes and is then poured into a mixture of ice and water (2 liters). The mixture is extracted three times with ether and the combined extracts are dried and evaporated to dryness. The residue is distilled and there is thus obtained 2,6-dichlorostyrene oxide, b.p. 74°–80° C./0.15 mm., m.p. 50°–52° C.

A mixture of the above compound (56.7 g.) and ethylenediamine (180 g.) is heated at 90° C. for 18 hours and then evaporated to dryness under reduced pressure. The residue is dissolved in chloroform, the solution is filtered and the filtrate is evaporated to dryness under reduced pressure. Ethyl acetimidate hydrochloride (37.1 g.) is added to a solution of the residue, which consists of 2-(β-aminoethylamino)-1-(2,6-dichlorophenyl)ethanol, in ethanol (300 ml.) and the mixture is heated under reflux for 2.5 hours and then evaporated to dryness under reduced pressure. The residue is stirred three times with ether (100 ml. each time), the ethereal solutions being discarded, and the solid residue is crystallised from isopropanol. There is thus obtained 3-β-2,6-dichlorophenyl-β-hydroxyethyl)-2-methyl-1-imidazoline hydrochloride, m.p. 221°–222° C.

A mixture of the above compound (15 g.) and thionyl chloride (75 ml.) is kept at laboratory temperature for 18 hours and then evaporated to dryness under reduced pressure. The residue is triturated with ether and then crystallised from a mixture of isopropanol and ether. There is thus obtained 3-β-chloro-β-2,6-dichlorophenylethyl)-2-methyl-1-imidazoline hydrochloride, m.p. 161° C. The free base is isolated from the hydrochloride by conventional means before use.

EXAMPLE 13

Anhydrous potassium carbonate (0.35 g.) is added to a solution of 6-(2,6-dichlorophenyl)-7-ethoxycarbonyl-2,3,5,6-tetrahydro-1H-pyrrolo[1,2-a]imidazole (0.09 g.) in methanol (3 ml.) and the mixture is heated under reflux for 90 minutes and then evaporated to dryness. The residue is dissolved in water and the solution is adjusted to pH 8 with aqueous 2N-hydrochloric acid, and extracted with ethyl acetate. The extract is dried and evaporated to dryness and the residue is dissolved in ethyl acetate and treated with an excess of ethereal hydrogen bromide. The mixture is evaporated to dryness and the residue is crystallised from isopropanol. There is thus obtained 6-(2,6-dichlorophenyl)-2,3,6,7-tetrahydro-5H-pyrrolo[1,2-a]-imidazole hydrobromide, m.p. 297°–299° C.

The 6-(2,6-dichlorophenyl)-7-ethoxycarbonyl-2,3,5,6-tetrahydro-1H-pyrrolo[1,2-a]imidazole used as starting material may be obtained as follows:

A mixture of 2-(β-aminoethylamino)-1-(2,6-dichlorophenyl)ethanol (2.49 g.), isopropyl (2-ethoxycarbonyl)acetimidate hydrochloride (2.5 g.) and ethanol (20 ml.) is stirred at laboratory temperature for 2 hours and then filtered and the filtrate is evaporated to dryness under reduced pressure. The residue is dissolved in aqueous 2N-hydrochloric acid and the solution is washed with ether and basified with aqueous sodium hydroxide solution. The solution is extracted with ethyl acetate and the extract is dried and evaporated to dryness. There is thus obtained as solid residue ethyl 1-(β-2,6-dichlorophenyl-β-hydroxyethyl)imidazolidin-2-ylideneacetate, m.p. 102°–105° C.

Methanesulphonyl chloride (0.172 ml.) is added dropwise during 5 minutes to a stirred mixture of the above compound (0.68 g.), triethylamine (0.42 ml.) and methylene chloride (10 ml.) which is cooled to 5° C., and the mixture is stirred for a further 5 minutes and then washed twice with ice-cold water, dried and evaporated to dryness. The residue is dissolved in dimethylformamide (3 ml.) and the solution is added dropwise to a stirred suspension of sodium hydride (0.15 g.) in dimethylformamide (3 ml.). The mixture is stirred at laboratory temperature for 1 hour and then at 60° C. for 1 hour, then poured into water and the mixture is extracted three times with ethyl acetate. The combined extracts are dried and evaporated to dryness and the residue is purified by thick-layer chromatography on silica gel plates using a mixture of 6:3:1 v/v/v toluene: ethyl acetate: triethylamine as eluant. There is thus obtained 6-(2,6-dichlorophenyl)-7-ethoxycarbonyl-2,3,5,6-tetrahydro-1H-pyrrolo[1,2-a]imidazole, m.p. 109°–112° C.

EXAMPLE 14

A solution of 6-(2,6-dichloro-3-nitrophenyl)-2,3,6,7-tetrahydro-5H-pyrrolo[1,2-a]imidazole hydrobromide (2.3 g.) in water (70 ml.) is shaken with hydrogen in the presence of a Raney nickel catalyst (0.5 g.) at laboratory temperature and atmospheric pressure until uptake of hydrogen ceases. The mixture is filtered, the filtrate is evaporated to dryness and the residue is dissolved in hot ethanol (200 ml.). The solution is concentrated to 20 ml. by distillation and then cooled and filtered. There is thus obtained as solid residue 6-(3-amino-2,6-dichlorophenyl)-2,3,6,7-tetrahydro-5H-pyrrolo-[1,2-a]imidazole hydrobromide, m.p. 275°–277° C.

What we claim is:

1. A compound selected from the group consisting of compounds of the formula:

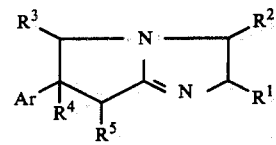

wherein $R^1$, $R^2$, $R^3$ and $R^5$, which may be the same or different, each is hydrogen or alkyl of up to 4 carbon atoms, and wherein Ar is phenyl, naphthyl, thienyl, pyridyl or furyl which bears a substituent in the position adjacent to the linking position which substitutent together with the substituent $R^4$ forms alkylene of up to 3 carbon atoms, and which nucleus Ar either bears no further substituent or bears one or two further substituents selected from halogen, amino, nitro, trifluoromethyl and alkyl, alkoxy, acylamino and dialkylamino each of up to 6 carbon atoms; and the pharmaceutically-acceptable acid-addition salts thereof.

2. A compound as claimed in claim 1 selected from the group consisting of compounds of the formula given in claim 1 wherein $R^1$, $R^2$, $R^3$ and $R^5$ are all hydrogen, Ar is phenyl and $R^4$ together with the substituent in the 2-position of the phenyl nucleus form ethylene, which phenyl nucleus Ar either bears no further substituent or bears a further substituent in the 3- or 6-position which is fluorine, chlorine, bromine, trifluoromethyl or alkyl or alkoxy each of up to 4 carbon atoms; and the pharmaceutically-acceptable acid-addition salts thereof.

3. A salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

4. The compound claimed in claim 1 which is (indane-1)spiro[6-(2,3,6,7-tetrahydro-5H-pyrrolo [1,2-a]imidazole)] or an acid-addition salt thereof.

5. A pharmaceutical composition having anti-hypertensive activity comprising an active ingredient an effective amount of at least one compound, or a pharmaceutically-acceptable acid-addition salt thereof, claimed in claim 1, in association with a pharmaceutically-acceptable carrier therefor.

6. A method for lowering blood pressure in a warm-blooded animal which comprises administering to said animal an effective amount of a compound claimed in claim 1.

* * * * *